United States Patent [19]

Zaby et al.

[11] Patent Number: 4,851,570

[45] Date of Patent: Jul. 25, 1989

[54] PROCESS FOR THE CONTINUOUS PRODUCTION OF MONO- AND POLYISOCYANATES

[75] Inventors: Gottfried Zaby, Leverkusen; Helmut Judat, Langenfeld; Siegbert Humburger, Leverkusen; Stefaan de Vos, St. Job; Rolf W. Eckermann, Bergisch Gladbach, all of Fed. Rep. of Germany

[73] Assignee: Bayer Aktiengesellschaft, Bayerwerk, Fed. Rep. of Germany

[21] Appl. No.: 263,154

[22] Filed: Oct. 27, 1988

[30] Foreign Application Priority Data

Oct. 31, 1987 [DE] Fed. Rep. of Germany ....... 3736988

[51] Int. Cl.$^4$ ............................................. C07C 71/00
[52] U.S. Cl. .................................................. 560/347
[58] Field of Search ...................................... 560/347

[56] References Cited

U.S. PATENT DOCUMENTS 3,781,320 12/1973 Irwin ..................................... 560/347
3,829,458 8/1974 Horn et al. ........................... 260/453

FOREIGN PATENT DOCUMENTS 844896 5/1952 Fed. Rep. of Germany .
1023000 3/1966 United Kingdom .

*Primary Examiner*—Alan Siegel
*Attorney, Agent, or Firm*—Gene Harsh; Joseph C. Gil; Richard E. L. Henderson

[57] ABSTRACT

This invention relates to a process for the continuous production of an organic monoisocyanate or polyisocyanate in a single stage reaction. A reaction mixture is formed by continuously mixing, at a temperature elevated above room temperature but not exceeding about 150° C., a solution in a substantially inert organic solvent of a monoamine or polyamine corresponding to the monoisocyanate or polyisocyanate and a solution in a substantially inert organic solvent of phosgene. The reaction mixture is continuously passed upwards from below through a reaction column comprising at least 10 separate chambers separated by perforated plates, wherein each perforation of said perforated plates has a diameter of less than about 20 mm.

12 Claims, No Drawings

PROCESS FOR THE CONTINUOUS PRODUCTION OF MONO- AND POLYISOCYANATES

BACKGROUND OF THE INVENTION

The present invention relates to a new continuous process for the production of mono- and polyisocyanates by the phosgenation of the corresponding mono- or polyamines wherein the reaction is carried out in special columns equipped with perforated plates.

The production of organic isocyanates by phosgenating the amines from which they are derived has hitherto been carried out in mixing tanks (e.g., DE-OS No. 1,468,445), cascades of mixing tanks (e.g., DE-PS No. 884,896), reaction columns filled with packing material (e.g., DE-OS No. 2,112,181) or empty columns (e.g. Ullmanns Encyclopädie der technischen Chemie, 4th Edition (1977), pages 351 et seq, in particular FIG. 2 on page 352). These methods frequently require integration of the apparatus in a circulating system for continuous operation (for example, in the process according to DE-OS No. 2,112,181) because a single passage through the reaction vessel is not sufficient for complete conversion.

It has now been found that a very significant improvement in the phosgenation reaction can be achieved by using special columns equipped with perforated plates through which the reaction mixture flows upwards from below. The process according to the invention described below is distinguished in particular by the following advantages:

In contrast to the columns with packing materials previously used, this reaction vessel does not clog.

Substantially higher volume/time yields can be obtained even at lower reaction temperatures than in the known processes using empty columns, thereby saving energy.

The yield of product is increased despite the comparatively low reaction temperatures and short residence times.

Circulation is unnecessary, thereby allowing use of simpler apparatus.

SUMMARY OF THE INVENTION

The present invention relates to a process for the continuous production of organic mono- or polyisocyanates in a single stage reaction wherein mono- or polyamines corresponding to the mono- or polyisocyanates to be produced are reacted as solutions in organic solvents with phosgene dissolved in organic solvents at temperatures which are elevated above room temperature but which remain below about 150° C. The reaction mixture obtained by continuously mixing the amine solution with the phosgene solution is continuously passed upwards from below through a reaction column comprising at least 10 chambers separated by perforated plates.

DESCRIPTION OF THE INVENTION

The process according to the invention enables any organic mono- or polyisocyanates to be prepared by phosgenating the corresponding mono- or polyamines. Examples of mono- or polyamines which may be used as starting materials include aniline, halogen-substituted anilines such as 4-chlorophenylamine, 1,6-diaminohexane, 1-isocyanato-3,3,5-trimethyl-5-(isocyanatomethyl)-cyclohexane, 2,4-diaminotoluene or commercially available mixtures thereof with 2,6-diaminotoluene, and polyamine mixtures of the diphenylmethane series obtainable by the known process of aniline formaldehyde condensation.

The process according to the invention is particularly advantageous for the phosgenation of 2,4-diaminotoluene or commercially available mixtures therefore with 2,6-diaminotoluene (generally containing up to 35% by weight of 2,6-diaminotoluene, based on the whole mixture), and polyamine mixtures of the diphenylmethane series.

The amines to be phosgenated may be used for the process according to the invention as solutions in substantially inert organic solvents. These amine solutions generally have an amine content of from 5 to 50, preferably 5 to 40 and most preferably 7 to 20 % by weight. Chlorobenzene, dichlorobenzene and mixtures thereof are preferred solvents.

In the process according to the invention., phosgene is used in the form of 30 to 75, preferably 30 to 65 and most preferably 40 to 65 % by weight solutions in substantially inert organic solvents, the solvent being preferably the same as that used for the amine.

The equivalent ratio of amine to phosgene is generally in the range of 1:1.5 to 1:7, preferably 1:2 to 1:5.

Known mixing apparatus may be used for mixing the amine solution with the phosgene solution, for example counterflow mixing chambers (DE-PS No. 1,146,872), rotary pumps (DE-PS No. 949,227 or DE-AS No. 2,153,268), venturi mixing nozzles (DE-AS No. 1,175,666 or U.S. Pat. No. 3,507,626), in-line mixers (U.S. Pat. No. 3,321,283) or tubular reactors (U.S. Pat. No. 3,226,410).

In the process according to the invention, the reaction mixture obtained by mixing the starting solutions is passed upwards from below through a reaction column (phosgenation tower) which is equipped with perforated plates so that the interior of the column is subdivided into at least 10 (preferably 20 to 50) chambers by horizontally installed perforated plates. It would be possible in principle, although by no means preferred, to use several columns of perforated plates connected in series comprising a total of 10 or more (preferably 20 to 50) chambers.

A higher degree of subdivision into chambers is not advantageous, first, because a cushion of gas forms beneath each perforated plate, thereby reducing the capacity of reaction chamber available to the solid and liquid components of the reaction mixture, and, second, because the additional improvement in the residence time is minimal.

The perforations of the perforated plates generally have a diameter of less than about 20 mm, preferably from 2 to 10 mm. The number of perforations is preferably chosen according to the throughput rate so that the reaction mixture ascending through the column will essentially be prevented from back mixing between the individual chambers.

The reaction mixture flowing upwards through the column of liquid components (solutions of the starting materials and of the isocyanates formed in the reaction), gaseous components (phosgene and hydrogen chloride being generated) and, at least at the beginning of the reaction, solid components (carbonyl chlorides and amine hydrochlorides suspended in solvent). Reaction conditions are optimum when the velocity of the ascending gaseous phase in the perforations of the plates is from 2 to 20 m/sec, preferably from 3.5 to 10 m/sec, and the velocity of the ascending liquid phase in the perforations of the plates is from 0.05 to 0.4 m/sec, preferably from 0.1 to 0.2 m/sec.

The temperature of the reaction mixture leaving the mixing apparatus is generally from 40° to 100° C., whereas the temperature at the head of the reaction column is below 150° C., preferably from 70° to 130° C. and more preferably from 90° to 125° C. This is generally achieved by suitably heating the reaction column. In order to minimize the volume required for phosgenation, the energy used to obtain the desired output temperature is advantgeously introduced in the lower region of the phosgenation tower or even at a point before the entrance into the reactor. This prevents part of the volume of the reactor from being ineffective due to excessively low temperature which could cause the overall reaction velocity to be too low.

The dimensions of the reaction column, the construction of the perforated plates, and the quantity of reaction mixture introduced into the column are generally selected to provide an average residence time of the reaction mixture in the reaction column of not more than 120 minutes, preferably not more than 60 minutes.

The pressure at the head of the reaction column is generally from 1.2 to 3 bar, preferably from 1.5 to 2.5 bar (abs.) but higher or lower pressures may be employed.

The reaction mixture of liquid and gaseous components leaving at the top end of the reaction column is first freed in known manner from gaseous components (excess phosgene and hydrogen chloride) and then worked up by distillation.

The invention, which is set forth in the foregoing disclosure, is not to be construed or limited either in spirit or in scope by these examples. Those skilled in the art will readily understand that known variations of the conditions of the following preparative procedures can be used. In the following examples, all percentages are percentages by weight and all temperatures are degrees Celsius unless otherwise noted.

DESCRIPTION OF THE PREFERRED EMBODIMENTS

In the following Examples, the diamine solutions and phosgene solutions were mixed together in a rotary pump modified according to DE-AS No. 2,153,268. The resulting solution-suspensions were introduced into the lower part of the reaction apparatus at a temperature of 70° to 90° C. The reaction apparatus used for the Comparison Examples was a conventional cascade composed of three reactors in series (reaction columns) which were free from internal installations and had a total volumn of 17 m³, similar to that described in Ullmanns Encyclopädie der technischen Chemie, 4th Edition (1977), FIG. 2, page 352. The reaction apparatus used for the Examples according to the invention was a reaction column with a total volumn of 7 m³ equipped with 23 perforated plates having perforations 10 mm in diameter.

A mixture of 65% of 2,4-diaminotoluene and 35% of 2,6-diaminotoluene ("TDA") was used as starting amine in all of the Examples.

The reaction mixture obtained at the head of the (last) reactor under a pressure of about 1.5 bar (abs.) in all of the Examples was in each case freed from gaseous constituents and then distilled.

EXAMPLE 1a (Comparison)

TDA (550 kg/h) dissolved in o-dichlorobenzene ("ODB") (7300 kg/h) mixed with 7070 kg/h of a 48% phosgene solution in ODB. The resulting solution-suspension was introduced into the heated reaction cascade in which the temperatures were adjusted to 80° C. at the head of the first reactor, 125° C. at the head of the second reactor, and 170° C. at the head of the third reactor. For an average residence time of 80 minutes, the yield of isomeric mixture of diisocyanato toluene ("TDI") corresponding to the starting amine was 95.8%.

EXAMPLE 1b (According to the invention)

Example 1a was repeated except that a reaction column according to the invention (phosgenation tower) was used. The lower part of the apparatus was heated so that the liquid reaction mixture overflowing from the head was at a temperature of about 115° C. The flow velocity of the gaseous phase through the individual perforations of the plates was 6.6 m/sec and the flow velocity of the liquid phase was about 0.18 m/sec. After an average residence time of 33 minutes, a TDI yield of 97.0% was obtained.

EXAMPLE 2a (Comparison)

Example 1a was repeated except that only 4450 kg/h of ODB was used to dissolve the diamine. After an average residence time of 100 minutes, a TDI yield of 94.5% was obtained.

EXAMPLE 2b (Comparison)

Example 1b was repeated except that only 4450 kg/h of ODB was used to dissolve the diamine. The flow velocity of the gaseous phase through the perforations of the plates was about 6.6 m/sec and that of the liquid phase was 0.14 m/sec. After an average residence time of 41 minutes, a TDI yield of 96.5% was achieved.

EXAMPLE 3a (Comparison)

Example 1a was repeated except that only 3120 kg/h of ODB was used to dissolve the TDA. After an average residence time of 113 minutes, a TDI yield of 93.3% was achieved.

EXAMPLE 3b (According to the invention)

Example 1b was repeated except that only 3120 kg/h of ODB was used to dissolve the diamine. The flow velocity of the gaseous phase through the perforations of the plates was about 6.6 m/sec and that of the liquid phase was about 0.12 m/sec. A TDI yield of 95.7% was obtained after an average residence time of 46 minutes.

EXAMPLE 4a (Comparison)

Example 1a was repeated except that 400 kg/h of TDA, 5300 kg/h of ODB for dissolving the TDA, and 5400 kg/h of the 48% phosgene solution were used.

After an average residence time of 107 minutes, a TDI yield of 96.1% was obtained.

EXAMPLE 4b (According to the invention)

When the same flow rates as in Example 4a were used in a reaction column according to the invention, a TDI yield of 97.0% was obtained after an average residence time of 44 minutes. The flow velocity of the gaseous phase through the perforations of the plates was about 4.8 m/sec and that of the liquid phase was about 0.13 m/sec.

EXAMPLE 5a (Comparison)

Example 1a was repeated except that 400 kg/h of TDA dissolved in 5300 kg/h of ODB and 2700 kg/h of a 48% phosgene solution were used. A TDI yield of 94.6% was obtained after an average residence time of 138 minutes.

EXAMPLE 5b (According to the invention)

When the same flow rates of material as in Example 5a were used in the column according to the invention, a TDI yield of 95.6% was obtained after an average residence time of 57 minutes. The flow velocity of the gaseous phase through the perforations of the plate was about 4.8 m/sec and that of the liquid phase was about 0.10 m/sec.

What is claimed is:

1. A process for the continuous production of an organic monoisocyanate or polyisocyanate in a single stage reaction comprising
   (a) forming a reaction mixture by continuously mixing, at a temperature elevated above room temperature but not exceeding about 50° C.,
      (i) a solution in a substantially inert organic solvent of a monoamine or polyamine corresponding to the monoisocyanate or polyisocyanate, and
      (ii) a solution in a substantially inert organic solvent of phosgene, and
   (b) continuously passing said reaction mixture upwards from below through a reaction column comprising at least 10 separate chambers separated by perforated plates, wherein each perforation of said perforated plates has a diameter of less than about 20 mm, or a series of such reaction columns comprising a total of at least 10 separate chambers.

2. A process according to claim 1 wherein the reaction mixture is continuously passed upwards through a reaction column comprising at least 10 separate chambers separated by perforated plates.

3. A process according to claim 2 wherein the reaction column comprises about 20 to 50 separate chambers separated by perforated plates.

4. A process according to claim 2 wherein each perforation of said perforated plates has a diameter of about 2 to 10 mm.

5. A process according to claim 2 wherein the number of said chambers and the number and size of said perforations is selected in such a way that liquid components of said reaction mixture ascend at a velocity of from about 0.05 to 0.4 m/sec.

6. A process according to claim 5 wherein gaseous components present in said reaction mixture ascend at a velocity of from about 2 to 20 m/sec.

7. A process according to claim 2 wherein the temperature is from 70° to 130° C.

8. A process according to claim 2 wherein the temperature is from 90° to 125° C.

9. A process according to claim 2 for the continuous production of an organic polyisocyanate wherein the polyamine is 2,4-diaminotoluene, a mixture of 2,4-diaminotoluene with 2,6-diaminotoluene, or a polyamine mixture of the diphenylmethane series.

10. A process according to claim 2 wherein the substantially inert solvent for each component is chlorobenzene or dichlorobenzene.

11. A process according to claim 2 for the continuous production of an organic polyisocyanate in a single stage reaction comprising
    (a) forming a reaction mixture by continuously mixing, at a temperature of from 90° to 125° C.,
       (i) a solution in chlorobenzene or dichlorobenzene of a polyamine corresponding to the polyisocyanate, and
       (ii) a solution in chlorobenzene or dichlorobenzene of phosgene, and
    (b) continuously passing said reaction mixture upwards from below through a reaction column comprising about 20 to 50 separate chambers separated by perforated plates, wherein each perforation of said perforated plates has a diameter of about 2 to 10 mm.

12. A process according to claim 1 wherein the reaction mixture is continuously passed upwards through a series of reaction columns comprising a total of at least 10 separate chambers.

* * * * *

UNITED STATES PATENT AND TRADEMARK OFFICE
CERTIFICATE OF CORRECTION

PATENT NO. : 4,851,570

DATED : JULY 25, 1989

INVENTOR(S) : GOTTFRIED ZABY ET AL

It is certified that error appears in the above-identified patent and that said Letters Patent is hereby corrected as shown below:

At Column 4, line 39, please correct "(Comparison)": to --According to the Invention --

At Column 5, line 39, please correct "$50^\circ C$" to --$150^\circ C$--

Signed and Sealed this

Eighth Day of June, 1993

Attest:

MICHAEL K. KIRK

Attesting Officer

Acting Commissioner of Patents and Trademarks